US012599299B2

(12) United States Patent
Ertl

(10) Patent No.: US 12,599,299 B2
(45) Date of Patent: Apr. 14, 2026

(54) METHOD AND APPARATUS FOR MULTIMODAL SOFT TISSUE DIAGNOSTICS

(71) Applicant: DENTSPLY SIRONA Inc., York, PA (US)

(72) Inventor: Thomas Ertl, Usingen (DE)

(73) Assignee: Dentsply Sirona Inc., York, PA (US)

( * ) Notice: Subject to any disclaimer, the term of this patent is extended or adjusted under 35 U.S.C. 154(b) by 494 days.

(21) Appl. No.: 17/927,054

(22) PCT Filed: May 20, 2021

(86) PCT No.: PCT/EP2021/063523
§ 371 (c)(1),
(2) Date: Nov. 22, 2022

(87) PCT Pub. No.: WO2021/239583
PCT Pub. Date: Dec. 2, 2021

(65) Prior Publication Data
US 2023/0222767 A1     Jul. 13, 2023

(30) Foreign Application Priority Data

May 26, 2020     (EP) ..................................... 20176399

(51) Int. Cl.
*A61B 5/00*         (2006.01)
*A61B 1/00*         (2006.01)
(Continued)

(52) U.S. Cl.
CPC .......... *A61B 1/24* (2013.01); *A61B 1/000094* (2022.02); *A61B 1/000096* (2022.02);
(Continued)

(58) Field of Classification Search
CPC ........ A61B 1/24; A61B 5/0035; A61B 5/0088
See application file for complete search history.

(56) References Cited

U.S. PATENT DOCUMENTS

| | | | |
|---|---|---|---|
| 2008/0118886 A1 | 5/2008 | Liang et al. | |
| 2009/0137908 A1* | 5/2009 | Patwardhan | ........... A61B 5/444 |
| | | | 600/476 |

(Continued)

FOREIGN PATENT DOCUMENTS

| | | |
|---|---|---|
| EP | 4157061 A2 | 4/2023 |
| JP | 2004237081 | 8/2004 |

(Continued)

OTHER PUBLICATIONS

"Japanese Application Serial No. 2022-572711, Notification of Reasons for Refusal mailed Mar. 4, 2025", w English translation, 12 pgs.

(Continued)

*Primary Examiner* — Joel F Brutus
(74) *Attorney, Agent, or Firm* — SCHWEGMAN LUNDBERG & WOESSNER, P.A.

(57) ABSTRACT

A method and device for multimodal imaging of dermal and mucosal lesions. The method includes using at least two imaging modalities from which one is a 3D scan of the lesion, and, additionally providing information on the distance and angulation between scanning device and the dermis or mucosa and mapping at least the second modality over the 3D data.

28 Claims, 5 Drawing Sheets

(51) Int. Cl.

| | |
|---|---|
| *A61B 1/24* | (2006.01) |
| *A61B 5/107* | (2006.01) |
| *G06T 7/30* | (2017.01) |
| *G06T 7/40* | (2017.01) |
| *G06V 10/764* | (2022.01) |

(52) U.S. Cl.

CPC .......... *A61B 5/0035* (2013.01); *A61B 5/0062* (2013.01); *A61B 5/0071* (2013.01); *A61B 5/0088* (2013.01); *A61B 5/1079* (2013.01); *G06T 7/30* (2017.01); *G06T 7/40* (2013.01); *G06V 10/764* (2022.01); *G06T 2207/10028* (2013.01); *G06T 2207/10064* (2013.01); *G06T 2207/10101* (2013.01); *G06T 2207/20081* (2013.01); *G06T 2207/20084* (2013.01); *G06T 2207/30096* (2013.01)

(56) References Cited

U.S. PATENT DOCUMENTS

| | | | |
|---|---|---|---|
| 2014/0022356 A1 | 1/2014 | Fisker et al. | |
| 2014/0267849 A1* | 9/2014 | Geelen ................. | G02B 3/0043 |
| | | | 348/278 |
| 2015/0133778 A1 | 5/2015 | Barriga Rivera et al. | |
| 2015/0164335 A1 | 6/2015 | Van Der Poel et al. | |
| 2016/0081553 A1 | 3/2016 | Weber et al. | |
| 2016/0157725 A1* | 6/2016 | Munoz ................... | H04N 23/51 |
| | | | 600/407 |
| 2016/0327779 A1* | 11/2016 | Hillman ............. | G02B 21/0032 |
| 2019/0053750 A1 | 2/2019 | Chandrakasan et al. | |
| 2019/0200006 A1 | 6/2019 | Fisker et al. | |
| 2019/0269485 A1 | 9/2019 | Elbaz et al. | |
| 2019/0336063 A1* | 11/2019 | Dascalu ............... | A61B 5/0064 |
| 2019/0350395 A1* | 11/2019 | Matsunaga Masaoka ................... | |
| | | | A47J 47/14 |
| 2019/0387972 A1* | 12/2019 | Hu ....................... | A61B 5/7214 |
| 2020/0126220 A1* | 4/2020 | Kashima .............. | A61B 1/0646 |

FOREIGN PATENT DOCUMENTS

| | | |
|---|---|---|
| JP | 2009501579 | 1/2009 |
| JP | 2015527896 | 9/2015 |
| JP | 2018514237 | 6/2018 |
| JP | 2018201648 | 12/2018 |
| JP | 2023527046 A | 6/2023 |
| WO | 2021239583 | 12/2021 |
| WO | WO-2021239583 A3 | 1/2022 |

OTHER PUBLICATIONS

"International Application Serial No. PCT EP2021 063523, International Search Report mailed Dec. 1, 2021", 7 pgs.

"International Application Serial No. PCT EP2021 063523, Written Opinion mailed Dec. 1, 2021".

"International Application Serial No. PCT EP2021 063523, International Preliminary Report on Patentability mailed Dec. 8, 2022".

International Search Report; PCT/EP2021063523; Nov. 19, 2021 (completed); Dec. 1, 2021 (mailed).

Written Opinion of the International Searching Authority; PCT/EP2021063523; Nov. 19, 2021 (completed); Dec. 1, 2021 (mailed).

"European Application Serial No. 21726924.0, Response to Communication pursuant to Rules 161(2) and 162 EPC filed Jun. 21, 2023", 36 pgs.

"International Application Serial No. PCT/EP2021/063523, Invitation to Pay Additional Fees mailed Aug. 10, 2021", 12 pgs.

"Chinese Application Serial No. 202180037988.7, Office Action mailed Jun. 18, 2025", 25 pgs.

"European Application Serial No. 21726924.0, Communication Pursuant to Article 94(3) EPC mailed Aug. 28, 2025", 6 pgs.

"Japanese Application Serial No. 2022-572711, Response filed Jun. 27, 2025 to Notification of Reasons for Refusal mailed Mar. 4, 2025", w/ English Claims, 12 pgs.

\* cited by examiner 1-1
FIG. 1
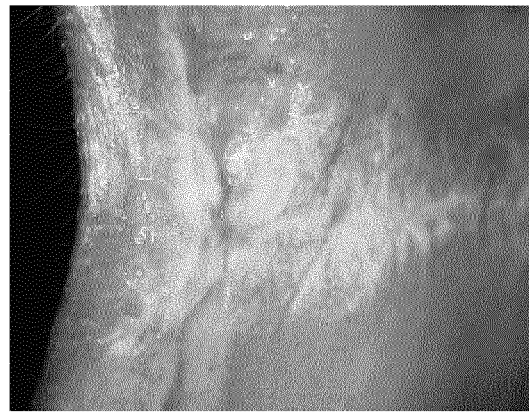
FIG. 2a
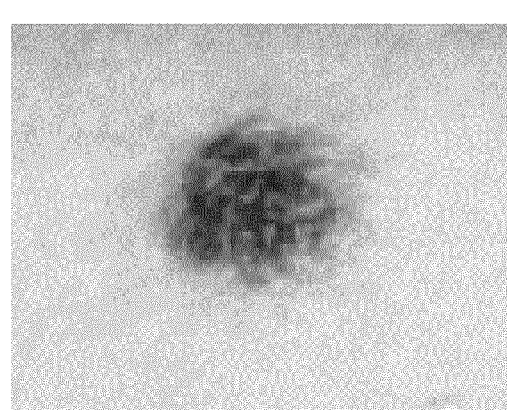
FIG. 2b

METHOD AND APPARATUS FOR MULTIMODAL SOFT TISSUE DIAGNOSTICS

CROSS-REFERENCE TO RELATED APPLICATIONS

This is a National Phase application of International Application No. PCT/EP2021/063523, filed May 20, 2021, which claims the benefit of and priority to European Application Ser. No. 20176399.2, filed on May 26, 2020, which are herein incorporated by reference for all purposes.

The Applicants herewith provide a statement of incorporation by reference under Rule 4.18 PCT that the priority application EP 20 176 399 is included into this international application through its entirety including the description, claims and drawings.

TECHNICAL FIELD OF THE INVENTION

The present invention relates to a method and apparatus for imaging of dermal and mucosal lesions.

BACKGROUND OF THE INVENTION

Traditional Soft Tissue Diagnostics

Diagnostics starts with patient anamnesis. Data are collected on the pre-disposition of the patient e.g. history of smoking, alcohol abuse, diabetes or injuries. Further it is important to assess the time of occurrence (typically more the time of detection by the patient) and progression of the lesion over time. Time can be days in case acute injuries with typical healing times or require an observation over years in case chronical soft tissue alterations as e.g. Lichen type lesions. Traditional oral soft tissue diagnostics relies on visual assessment of the lesion in combination with other information as tactile information or removability of whitish discolorations. For visual assessment several factors are important. The location and size of the lesion, the color of the lesion (redness, whitish discoloration), the structure and homogeneity of the discoloration (spot, network etc.). The doctor typically compares the actual lesion with either photos in oral disease teaching books, or other cases observed during practicing with known diagnosis. Additionally, the consistency of the mucosa is assessed by palpation as well as the relation to the underlying bone. (Is it possible to dislocate with slight pressure the lesion versus the bone or is the lesion fixed to the bone or underlying structures e.g. muscles) Further the removal of whitish discoloration with mechanical rubbing is tested to differentiate between candidiasis or leukoplakia type lesions. Involvement of bone may require additional x-ray diagnostics, e.g. in case of a tumor/swelling. Gold standard is still the histology taken from biopsy material.

Extended Diagnostics

Additionally, to the "conventional diagnosis" some dentists use Blue/UV light to excite tissue auto-fluorescence and diagnose the fluorescent image (e.g. Vizilite, VEL Scope or similar) or use staining with Toluidin blue. For oral auto-fluorescence diagnostics a light source is used to excite endogenous fluorophores such as nicotinamide adenine dinucleotide (NADH) and flavin adenine dinucleotide (FAD). For excitation wavelength in the UV/Blue range are used (375 and 440 nm). Emission is observed in the green wavelength range. Healthy mucosa emits a pale green auto-fluorescence when viewed with a narrowband filter suppressing the excitation wavelength. Dysplastic tissues show less fluorescence and appear darker in comparison to the surrounding healthy tissue. (see (1) in FIG. 1). Differentiation capability between dysplasia and benign inflammatory lesions is questioned in literature. Benign tissue inflammation shows often an increased blood supply to a lesion. The increased hemoglobin content may absorb both excitation and emission light and cause an intensity loss in the fluorescent image, which might be falsely attributed to neoplasia. Vizilite uses chemical agents to produce the excitation light. To activate it, a capsule is bent for breaking the glass vial, so that the chemical products react with each other and produce a bluish-white light with a wavelength of 430-580 nm, that lasts for around 10 min. The VELscope utilizes blue light excitation between 400 and 460 nm wavelength. The field of interest is observed through an optical imaging system. (see FIG. 1). A meta-analysis of 20 studies on auto-fluorescence methods for oral dysplasia detection (see reference document 1) shows large variations of sensitivity and specificity between different publications.

Vizilight: Comparing different studies Sensitivity and Specificity for Vizilight vary between 77%-100% (Sens) and 0%-28% (Spec). For the VELscope system sensitivity of 22%-100% and specificity of 16%-100% is reported. As an example, sensitivity and specificity of toluidine blue were determined to be 86.36% and 76.9% respectively. Another, non-optical method is the Oral CDx system. With a small brush, surface cells are collected and analysed in the laboratory. Sensitivity varies in different studies between 71.4-100% and specificity between 32-100%.

Summarized using auto-fluorescence alone seems to be not sufficient as diagnostic aid especially when considering the low prevalence of malignancies and variances of experience of users but can be one additional diagnostic tool in combination with others. Other methods as staining or brush biopsies show moderate (staining) or high variations in sensitivity and specificity. Therefore, an improvement of the diagnostic capabilities is desirable.

Neuronal Networks for Oral Disease Detection

Artificial intelligence is becoming more and more successful as diagnostic support for classification of dermal lesions and x-ray images. AI networks can for example achieve already the accuracy level of board certified dermatologists when using >100 k images for 700 disease classes for training. (See reference document 2). This results in ~150 images per class. An overview article on the usage of deep learning algorithms in dentistry reviewed 25 articles. As diagnostic modalities 2D x-ray, CBCT, QLF and OCT were used. A conclusion of this review is, that the typical data set size has an increasing trend starting with around 100 data sets per class up to 1000 data sets. 1000 data sets are reported to achieve around 98% accuracy and more than 4000 data sets are needed for an accuracy of more than 99%. Only one of the reviewed articles refers to gingivitis detection using QLF and classification by a CNN. No article refers to intra-oral disease classification. (Reference document 3). Aside the purely image related classification other authors report on the usage of CNNs including contextual factors in the detection of oral cancer. With a selection of 12 of 35 relevant factors adding risk factors, socio-economic factors to the clinical symptoms and history, a classification accuracy of 99% was achieved. (Reference document 4). In conclusion neural networks can contribute to improved medical and dental diagnostics, if a data base with sufficient sample size, features and quality is available.

Reference document 1: Efficacy of light based detection systems for early detection of oral cancer and oral potentially malignant disorders: Systematic review Ravleen Nagi, Yashoda-Bhoomi Reddy-Kantharaj, Nagaraju Rakesh, Sujatha Janardhan-Reddy, Shashikant Sahu Med Oral Patol Oral Cir Bucal. 2016 Jul. 1; 21 (4):e447-55.

Reference document 2: Dermatologist-level classification of skin cancer with deep neural networks Esteva A. et al. Nature 542 115-118(2017).

Reference document 3: An overview of deep learning in the field of dentistry Jae-Joon Hwang 1, Yun-Hoa Jung 1, Bong-Hae Cho 1, Min-Suk Heo 2, Imaging Science in Dentistry 2019; 49: 1-7.

Reference document 4: Usage of Probabilistic and General Regression Neural Network for Early Detection and Prevention of Oral Cancer Neha Sharma, Hari Om The Scientific World Journal Vol. 2015, Article ID 234191, http://dx.doi.org/10.1155/2015/234191.

Reference document 5: UV-angeregte Autofluoreszenz: Spektroskopische and fluoreszenzmikroskopische Untersuchungen zur Tumorselektivität endogener Gewebefarbstoffe Alexander Hohla Dissertation, LMU, Munchen, 2003.

SUMMARY OF THE INVENTION

In studies using neuronal network the lacking consistency of images of the region of interest is a point of concern and requires often manual preprocessing of the images. Photos are often taken from different distances (thus different magnifications), different observation angles and different lighting conditions. For multimodal diagnostics it is further important to achieve a good match (ideally pixel to pixel) between the different diagnostic modalities.

This invention addresses all these concerns and can avoid manual preprocessing and reduce computational time for AI classification of dermal and mucosal lesions.

An objective the present invention is to overcome at least some of the above mentioned problems. This objective has been achieved by the apparatus as defined in claim 1 and the method as defined in claim 28. The other claims relate to further embodiments and developments. Using a device that generates a precise 3D surface representation based e.g. on confocal, preferably chromatic confocal, time of flight, stereogrammetry or OCT technology has the advantage of knowing exactly the dimension of the lesion. The distance between the scanned surface and the 3D imaging device is always exactly known, thus the exact dimension of the lesion can be calculated. Further known is the angulation of the 3D imaging device against the scanned surface and the lighting conditions are always the same, since the illumination is integrated in the device. For 3D measurement this is typically a well-defined light pattern. Combining the 3D measurement with a spectrally resolved 2D image (e.g. 3 channels (RGB) or more) allows matching of 2D and 3D data. So far unknown in prior art is the use of the 3D texture for diagnostic purposes for soft tissue/mucosal lesions and the mapping of spectrally resolved 2D image data over the 3D texture of such lesions.

Most actual 3D scanning devices use a video like scanning technology that combines many sequentially acquired single 3D images and overlays them using 3D landmarks for correctly overlaying the single images. This is easy for e.g. teeth in the oral cavity but gets more difficult if the surface with the capture region of a single image shows not enough 3D landmarks. For instance as extreme cases a flat surface or a sphere cannot be scanned. In such a case with no or few landmarks the spectrally resolved 2D data superimposed to the 3D data can support the correct registration of single 3D images to each other.

This is helpful when scanning dermis or mucosa in flat areas, since lesions show a different scattering and absorption coefficient distribution than healthy tissue, which results for instance in a whitish coloration pattern when the scattering coefficient is increased or brownish coloration, if the absorption coefficient is increased. (See FIG. 2a whitish discoloration and see FIG. 2b: brownish discoloration).

Resolution of the 3D Images

With actual 3D scanning systems used e.g. in dental applications a resolution of 10 $\mu$m-30 $\mu$m is practically possible with an error in the same order. This is below the resolution of microscopes used for diagnosing histologies, but much better than the in-vivo visual inspection. This allows to calculate the surface texture of the lesion.

Wavelength Selection for 3D Image Generation:

Since biological tissue typically shows a lower penetration depth of the illumination light in the blue or near UV region (350 nm-400 nm) mainly due to the increased light scattering coefficient these wavelength can be used to produce a crisp surface texture 3D image in combination with a scanning methodology that suppresses volume scattered light (e.g. confocal and OCT based methods, which might be combined with depth of focus based technologies).

With wavelength longer than 840 nm, preferably longer than 980 nm, most preferable in the range of 1300 nm-1600 nm the scattering coefficient is much lower and allows 3D imaging into a depth of several 10th of mm up to few hundreds' micrometer. Then sub-surface structure acquisition and imaging becomes possible.

Providing at least two wavelength, one in the range of 350 and 400 nm and the other longer than 840 nm crisp 3D surface scanning can be combined with at least few hundreds of micrometer in-depth structural information of a dermal/mucosal lesion. In the easiest case the illumination is switched sequentially between different wavelengths and the illumination light sources are coupled into the same light path with dichroitic mirrors. This variant would work for wavelength that can be detected with the same sensor (e.g. CMOS 350 nm-~1000 nm).

For some 3D measurement technologies even the use of a not fully congruent light pass of the different wavelength can be possible, if the light source dimensions are small enough (e.g. LEDs). Then the slight angular deviation will cause a displacement of the illumination pattern on the sensor, but this can be corrected by calculation (displacement and distortion correction).

In case a second sensor is needed which would be the case when using illumination wavelength beyond 1000 nm, at least one beam splitters can be used to separate the optical path for the different sensors (see FIG. 3).

Fluorescent Imaging

A further extension of 3D imaging is the combination with fluorescence imaging. As described in the introduction human tissue is showing auto-fluorescence when exciting with the appropriate wavelength. Dermal/mucosal Lesions show different intensities of auto-fluorescence. This can be excitation in the UV/Blue range for FAD, NADH and collagen but as well red excitation to excite porphyrins. In combination with 3D imaging this allows the overlay of fluorescence image data over the 3D texture data.

The optical ray path can be conventional with a blocking filter for the excitation light using the same light pattern with UV/Blue wavelength as used for the 3D imaging and introducing the blocking filter for fluorescence detection in the imaging path after separation from the illumination path. However this would require a moving part (the filter) in the device. Further stronger excitation light power might be needed, depending on the design of the 3D scanner that is planned to be extended.

Giving up the 3D information in the fluorescent image data, the 3D optical path can stay unaltered. A UV blocking filter can be introduced in the 2D light path used typically for a 2D image in the visible spectral range, but still using the excitation light path of the 3D imaging illumination. (see FIG. 4)

A most preferable solution is however to use a separate excitation light source placed on the side of a replaceable hood. The blocking filter can be integrated in the window of the hood. Then the filter should not suppress the structured light for the 3D measurement. (FIG. 5). This is possible since many fluorophores of the human body e.g. collagen, NADH, FAD, Elastin and Keratin can be excited below 350 nm, and the 3D light pattern can use the range of 365 nm-405 nm. (Reference document 5). (see FIG. 6).

Another option is to place the excitation light blocking filter in the front of the 2D sensor and leaving the 3D light path unaltered. The filter does not affect the imaging in the visual range which is typically used to produce "color 2D images" since the fluorescence emission is in the visual range as well. (see FIG. 4).

This modified hood replaces the conventional hood, which is removable for sterilization anyway.

As example, but not limited to, the capabilities of an Intraoral 3D scanning device as e.g. Primescan or Omnicam (and other volume scattering resistant scanning devices) can be extended with the above described technologies.

Alternatively, the excitation LEDs can be placed inside the hood, and the hood is more or less an empty shell, which can be sterilized without reducing the lifetime of the LEDs, which requires however more modifications to existing 3D scanning devices.

A further advantage using Intra-oral scanning devices as basis for detecting and classifying intra-oral lesions is the form of the device, which allows access to all areas of the oral cavities, much different to devices for capturing images of lesions in dermatology.

The following preferred multimodal imaging options become possible with the above described technique:

Use of visual wavelength 2D images together with 3D information to calculate the magnification, distance and angulation of the lesion;

Visual wavelength 2D image overlaid over the 3D texture of the lesion;

Use of visual wavelength 2D images+fluorescent image with 3D information used for recalculation of the magnification, distance and angulation;

Visual wavelength 2D image+fluorescent image overlaid over the 3D texture of the lesion;

Visual wavelength 2D image overlaid over the 3D texture of the lesion+subsurface structure information;

Visual wavelength 2D image+fluorescent image overlaid over the 3D texture of the lesion+subsurface structure information;

not excluding however any other combination of the different imaging modalities, 2D color image, 3D texture image, Fluorescent image, subsurface image with long wavelength (see FIG. 7).

A further advantage of the absolute dimensions and known imaging conditions provided by the combination of at least 3D measurement and 2D color image allows to overlay (register) images of the same lesion taken at different times with a best fit algorithm to see even small deviations, which allows to monitor the development of a lesion over time.

The images captured with such a device can be processed on a processing means such as a computer being part of the device and presented to the doctor for visual inspection on a computer screen or can be used to build up a multimodal image database for training of a neuronal network (either an external network via a cloud based network training service or, if enough computational power is available an internal network), either alone or in combination with further "non-imaging" information as palpation results, removability of whitish layers, lesion history and risk factors (smoking, alcohol etc.). The screen may be a display of a desktop or mobile device with or without a touch screen, or may be a wearable device such as a head mounted display.

The trained network can be implemented in the device to provide diagnostic proposals or a recommendation to send the patient for further examination/biopsy to an oral disease specialist, if no conclusive diagnostic proposal can be given. (see FIG. 8).

BRIEF DESCRIPTION OF THE DRAWINGS

In the subsequent description, further aspects and advantageous effects of the present invention will be described in more detail by using exemplary embodiments and by reference to the drawings, wherein FIG. 1: shows a comparison of photographs and corresponding auto-fluorescence images;

FIG. 2a: shows a whitish colored lesion;

FIG. 2b: shows a lesion with increased pigmentation;

DETAILED DESCRIPTION OF THE INVENTION

Figure 3:
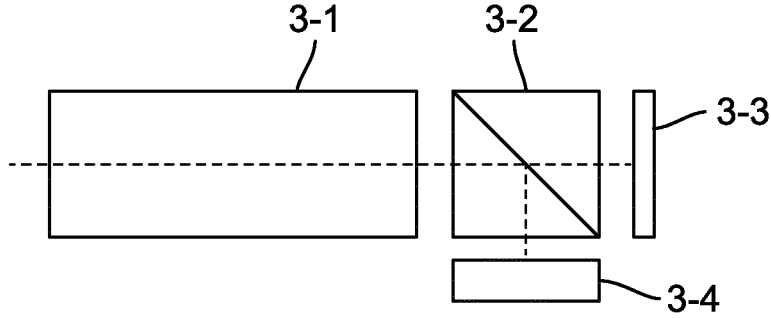
FIG. 3: shows core functional blocks of a 3D scanning device.

The reference numbers shown in the drawings denote the elements as listed below and will be referred to in the subsequent description of the exemplary embodiment.

1-1: Lesion
3-1: 3D scanning optics
3-2: Dichroitic mirror/Beam splitter
3-3: Sensor (e.g. CMOS)
3-4: Sensor (e.g. InGaAs Detector)
4-1: 3D scanning optics
4-2: Beam splitter
4-3: Sensor (e.g. CMOS)
4-4: Blocking filter
4-5: Sensor (e.g. CMOS)
4-6: Frontend
5-1: frontend hood

5-2: UV LED
5-3: Imaging window
7-1: 2D color image
7-2: Auto-fluorescence image
7-3: 3D texture image
7-4: Subsurface structure image
8-1: Device
8-2: 2D image
8-3: Data base
8-4: brush biopsy
8-5: X-ray image
8-6: Palpation result FIG. 1 shows a comparison of photographs and corresponding auto-fluorescence images, in this case made with a "VELscope" device. The corresponding images show clearly a better contrast between the lesion (1-1) and healthy tissue in the auto-fluorescence image.

FIG. 2a shows a white colored lesion mainly caused by thickening of the epidermal layer and thus significantly increased scattering coefficient, while FIG. 2b shows a lesion with increased pigmentation, which causes an increased absorption coefficient.

FIG. 3 shows functional blocks of a 3D scanning device. (3-1) is the 3D scanning optics, (3-2) is a dichroitic mirror/beam splitter separating the wavelength bands in a range from 300 nm-800 nm reaching a CMOS sensor (3-3), while wavelength longer than 1000 nm are mirrored to sensor (3-4), which can be an InGaAs Detector covering at least the wavelength range from 1000 nm-1600 nm.

Figure 4:
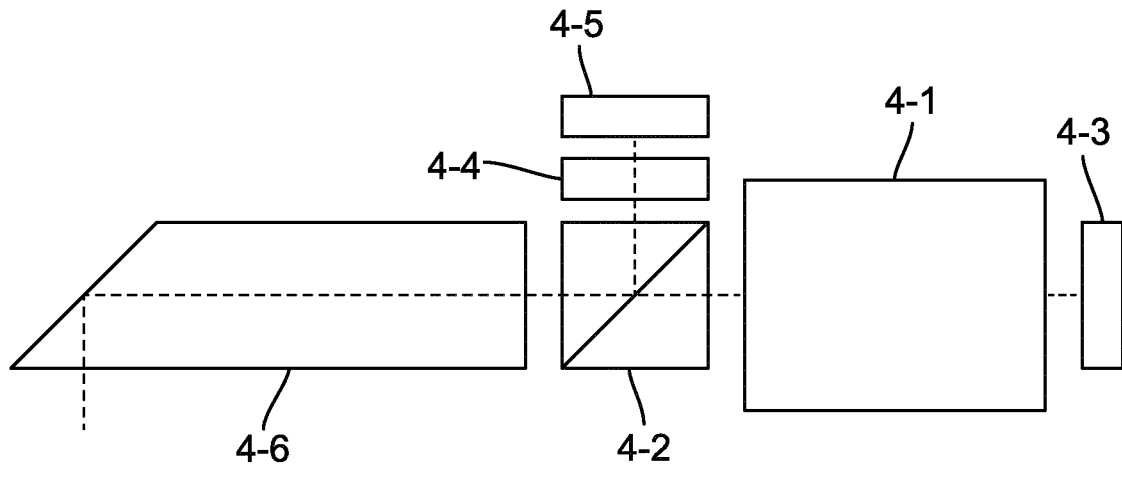
FIG. 4: shows functional blocks of a 3D scanning device.
Figure 6:
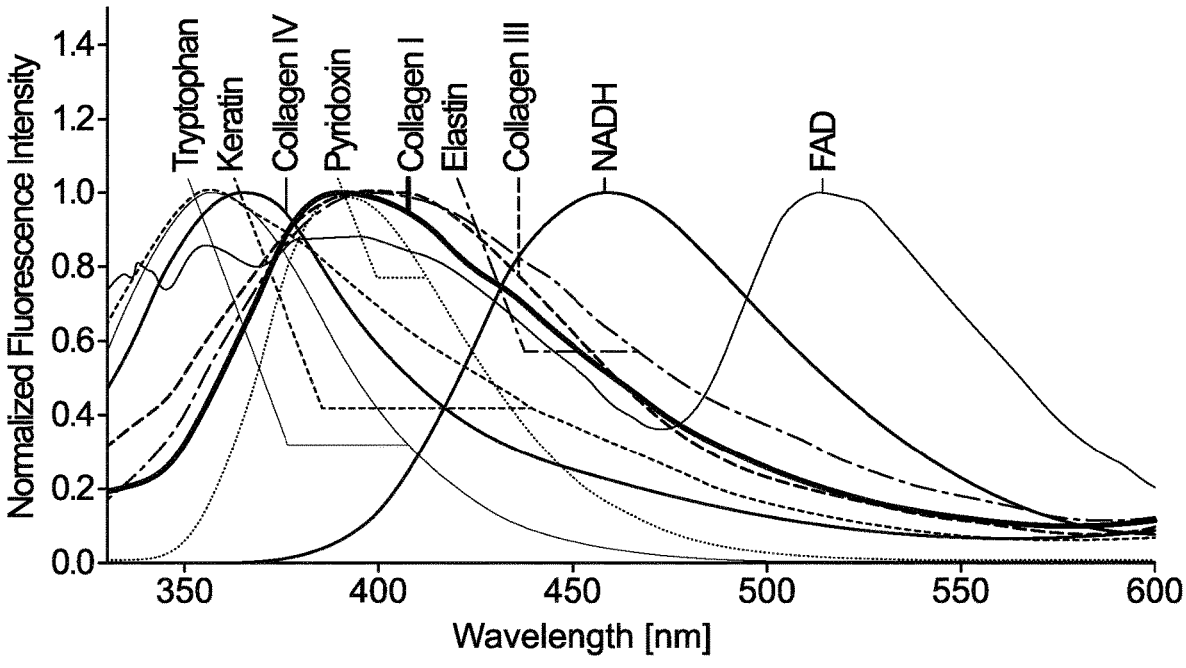
FIG. 6: shows emission bands of different fluorophores.

FIG. 4 shows functional blocks of a 3D scanning device. (4-6) is the frontend which deflects the image towards a beam splitter (4-2), separating the 2D imaging path from the 3D imaging path. (4-1) is the 3D scanning optics with a CMOS sensor (4-3) (as a 3D sensor) and (4-4) is a blocking filter that suppresses the excitation light not reaching the CMOS sensor (4-5). Alternatively the CMOS sensor (4-3) may be optionally replaced with a CQD Sensor (4-3) with extended sensitivity in the NIR range. Cutoff wavelength of the blocking filter is around 370 nm-400 nm. This allows the emission light of the auto-fluorescence to pass and allows as well the visual wavelength to pass for a color image. CMOS sensor (4-5) is not limited to traditional RGB 3 channel sensors but may contain more channels with better spectral resolution e.g. a mosaic type CMOS sensor with a multitude of different filters in combination with a lens array not shown in the image. This allows to differentiate between different fluorophores as shown in FIG. 6, since they have emission bands with maxima at different wavelength. The optical components (3-2), (3-3), and (3-4) in FIG. 3 can replace the component (4-5) in FIG. 4 in order to have a 2D sensor (3-3) for the visible range and another 2D sensor (3-4) for the NIR light.

The apparatus for multimodal imaging of dermal and mucosal lesions, comprises: a scanning device (8-1) having illumination light sources and sensors (3-3,3-4,4-3,4-5); and at least one processing means for calculation of images from raw data provided by the scanning device (8-1) which is adapted to use at least two imaging modalities from which the first imaging modality generates 3D data for a 3D image (7-3;7-4) in a 3D scan of the lesion, wherein the processing means is adapted to additionally provide 3D information on the distance and angulation between scanning device (8-1) and the dermis or mucosa through the use of an illumination pattern, or stereogrammetry, or time of flight, and map at least an image (7-1;7-2) generated by the second imaging modality over the 3D image (7-3;7-4) of the 3D scan based on the 3D information. The use of illumination pattern, or stereogrammetry, or time of flight are one of various techniques which can be used by those skilled in the art.

Figure 5:
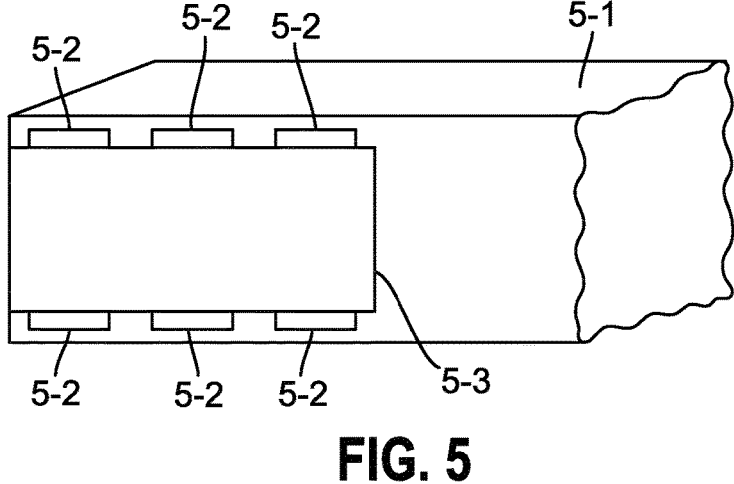
FIG. 5: shows a frontend hood of a 3D scanning device.

FIG. 5. shows the frontend hood (5-1) of a 3D scanning device. The hood is typically removable from the rest of the scanning device for disinfection. UV LEDs (5-2) are positioned parallel to the imaging window (5-3) to illuminate the field of interest and excite auto-fluorescence. The backscattered light passes through the imaging window (5-3) which can be covered already with an excitation light blocking filter (interference filter), if this filter is not positioned somewhere else in the detection ray path. The hood may contain the optical elements including the UV LEDs or may be a more or less empty shell covering the optics inside the hood. This avoids subjecting the UV LEDs to sterilization cycles.

FIG. 6 shows the different emission bands and maxima of different fluorophores excited in this case at 308 nm. The different peaks may allow a separation of different fluorophores. However, this is a normalized image. In reality the emission intensity of collagen is forming a high background signal that can dominate other fluorophores.

Figure 7:
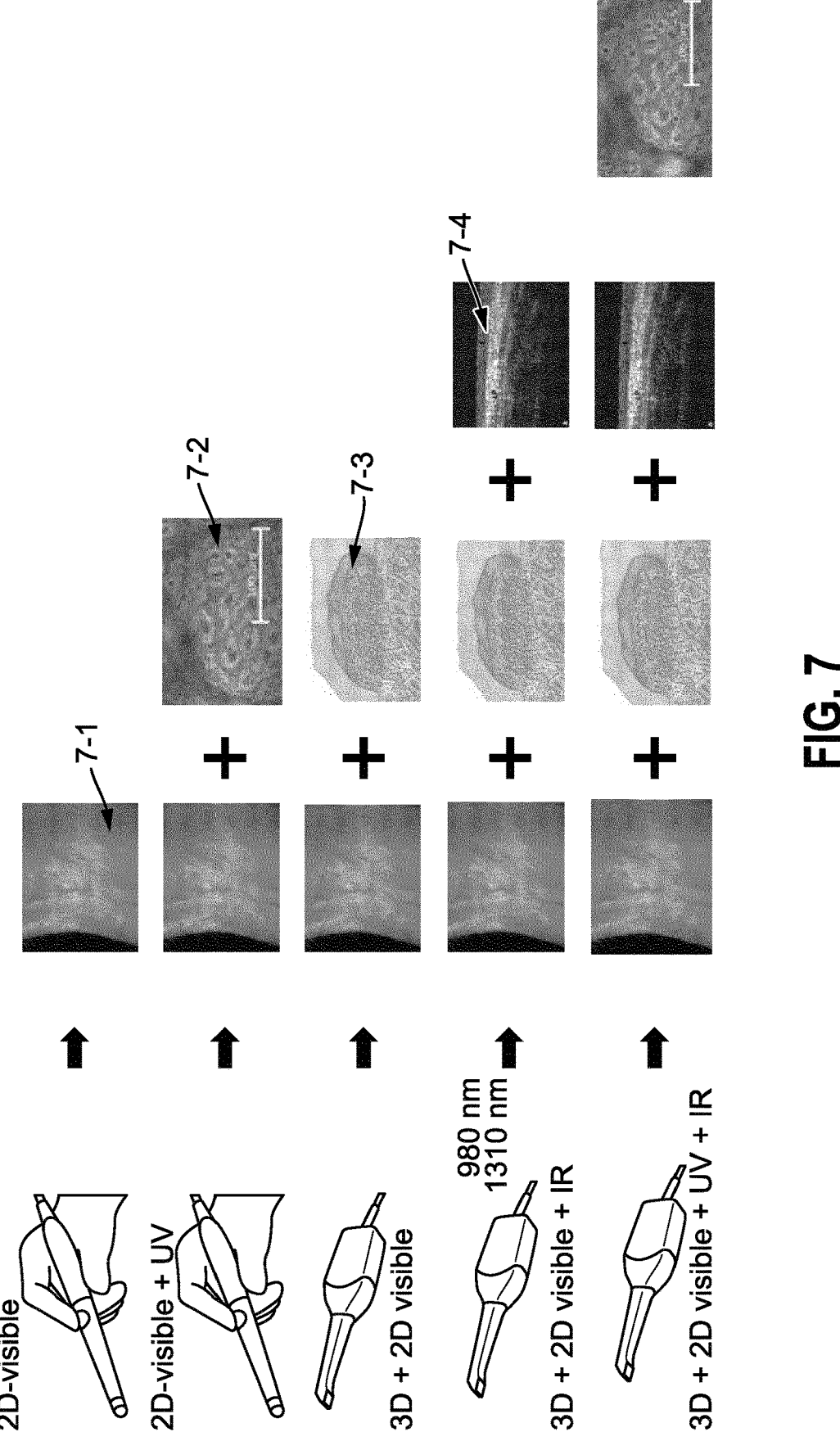
FIG. 7: shows combinations of imaging modalities.

FIG. 7 shows different combinations of imaging modalities possible with the proposed device, with 2D color images (7-1) (e.g., 2D spectrally resolved image), auto-fluorescence images (7-2), 3D texture images (7-3) and subsurface structure images (7-4) taken with longer wavelength.

Figure 8:
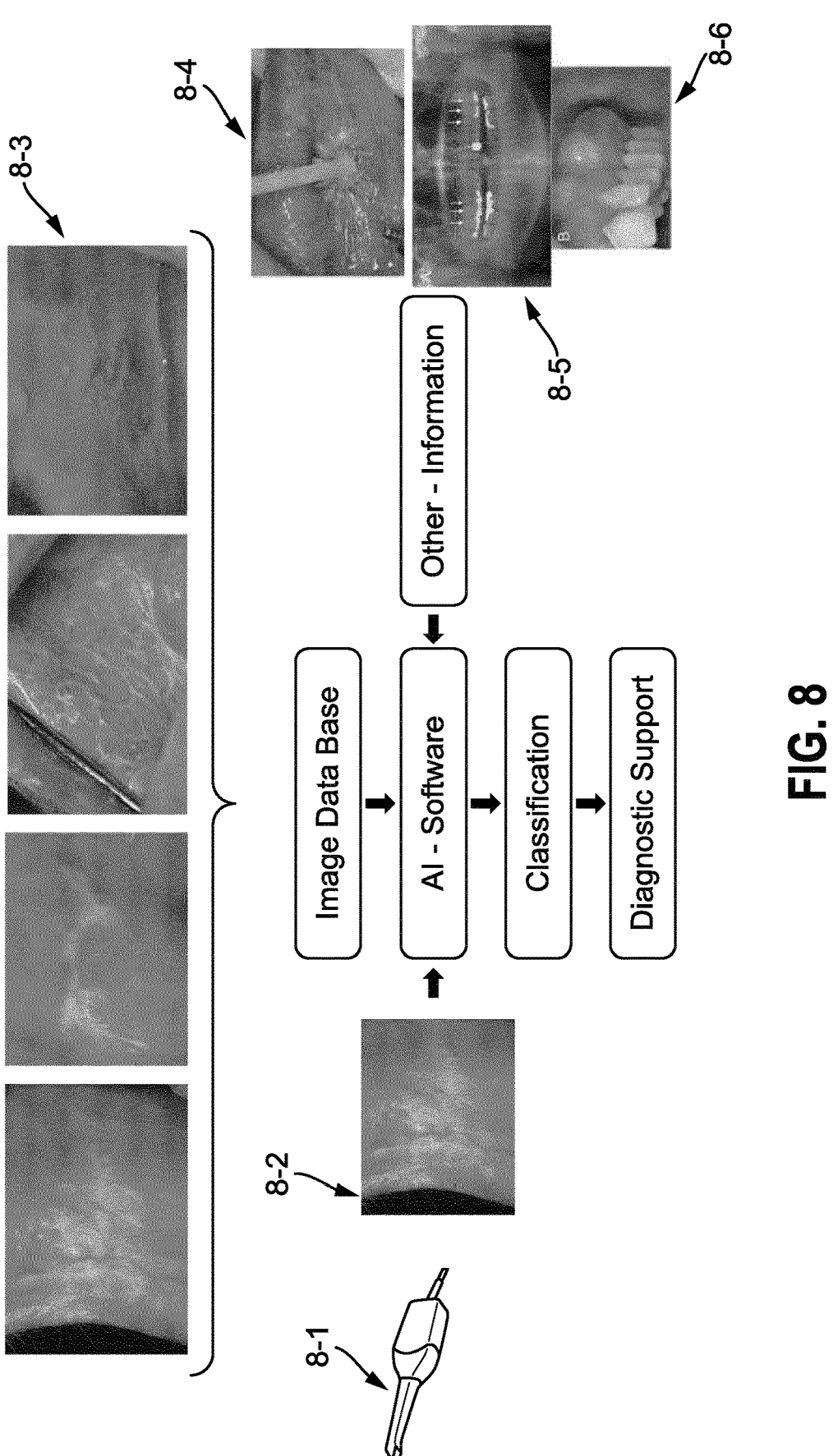
FIG. 8: shows a setup with artificial neuronal networks for diagnostic support.

FIG. 8 shows a setup how to use artificial neuronal networks for supporting the diagnosis of dermal/mucosal lesions with images taken with the proposed device (8-1). FIG. 8 shows only 2D images (8-2) which contain additional 3D information as distance, angulation, but it is not limited to these images. All combinations as shown in FIG. 7 or described in the text apply. From 2D images (8-2) a data base (8-3) is build, which is used for training of the artificial neuronal network. To improve the classification performance other than image data can be added as further information to the network as brush biopsy (8-4) results, x-ray images (8-5) and palpation results (8-6). Image for palpation results (8-6) is only exemplary chosen to show an elevation in the gingiva, which might be hard or soft. Of course, a multitude of cases with these data have to be included in the database connected to the corresponding case images, which are used for training.

With the present invention, due to the known exact absolute dimensions and known imaging conditions like angulation and distance of the lesion surface versus the imaging plane provided by the combination of at least 3D measurement and 2D color image allows to overlay (register) images of the same lesion taken at different times to see even small deviations, which allows to monitor the development of a lesion over time.

The invention claimed is:

1. An apparatus for multimodal imaging of a dermal or mucosal lesion comprising:

a scanning device having illumination light sources, a beam splitter, and sensors, the sensors including a visible light 2D sensor and an infrared light 3D sensor, and the beam splitter being configured to spectrally split detected light into wavelengths appropriate for the visible light 2D sensor and the infrared light 3D sensor; and at least one processor configured to:
compute images from raw data provided by the scanning device which is adapted to use at least two imaging modalities from which a first imaging modality generates 3D data for a 3D image in a 3D scan of a lesion,

compute 3D information on a distance and angulation between the scanning device and a dermis or mucosa, and map at least an image generated by a second imaging modality over the 3D image of the 3D scan based on the 3D information.

2. The apparatus of claim 1, wherein the at least one processor is further configured to compute exact dimensions of the lesion by using the 3D information on the distance and angulation between the scanning device and the lesion.

3. The apparatus of claim 1, wherein the at least one processor is further configured to compute a 3D surface texture of the lesion by using the 3D information of the 3D scan.

4. The apparatus of claim 1, wherein the second imaging modality generates as the image at least one of a 2D image or an auto-fluorescence image by employing one sensor, wherein the 2D image is spectrally resolved with 3 or more channels.

5. The apparatus of claim 4, wherein spectrally resolved 2D data of the 2D image that is superimposed through the at least one processor onto the 3D data to support a correct registration of 3D images of the 3D data to form a complete 3D image of a region of interest, wherein the 3D images include at least one of a 3D texture image or subsurface structure image.

6. The apparatus of claim 4, wherein the scanning device comprises a mosaic type CMOS sensor with a plurality of different filters in combination with a lens array configured for 2D spectral imaging.

7. The apparatus of claim 1, wherein the apparatus is configured to capture 3D data of the 3D scan with a technology that suppresses volume scattering through confocal imaging, Optical Coherence Tomography (OCT), or combinations of confocal scanning or OCT with depth of focus based technologies.

8. The apparatus of claim 1, wherein (i) the scanning device is configured to use wavelengths between 350 and 400 nm for the 3D scan of a surface by employing one corresponding sensor for the 3D image or (ii) the scanning device is configured to use a wavelength longer than 840 nm for the 3D scan of a subsurface by employing one corresponding sensor for a subsurface structure image so as to operate at wavelength where dermal and mucosal lesions show a smaller scattering coefficient.

9. The apparatus of claim 8, wherein the scanning device is configured to use both wavelength ranges together for 3D scan of the surface and 3D scan of the subsurface.

10. The apparatus of claim 9, wherein the scanning device is configured to switch an illumination sequentially between different wavelengths, wherein the illumination light sources are coupled into the same light path with dichroitic mirrors.

11. The apparatus of claim 9, wherein a light path of illumination sources for different wavelengths is not fully congruent, provided that light source dimensions are small enough and slight angular deviation causing a displacement of an illumination pattern on associated sensor is corrected by calculation.

12. The apparatus of claim 9, wherein in the scanning device when using illumination with wavelength beyond 1000 nm, the scanning device comprises at least one beam splitter configured to separate an optical path for different sensors.

13. The apparatus of claim 1, wherein the first imaging modality or the second imaging modality is further configured for fluorescence imaging with excitation light in a UV/Blue range for fluorophores including flavin adenine dinucleotide (FAD), nicotinamide adenine dinucleotide (NADH), and collagen.

14. The apparatus of claim 13, wherein the scanning device comprises a blocking filter for excitation light using a same illumination pattern with a UV/Blue wavelength as used for 3D imaging and adapted to introduce a blocking filter for fluorescence detection into an imaging path after separation from the illumination path.

15. The apparatus of claim 14, wherein the blocking filter is in a 2D imaging path for a 2D image of the second imaging modality.

16. The apparatus of claim 15, wherein the blocking filter is placed in front of one 2D sensor for the 2D image.

17. The apparatus of claim 13, wherein the scanning device comprises a separate excitation light source placed on sides of a replaceable hood and a blocking filter is integrated in a window of the replaceable hood and the blocking filter is designed not to suppress structured light for 3D measurement.

18. The apparatus of claim 17, wherein the replaceable hood covers fluorescence excitation LEDs to illuminate a field of interest through the window wherein the replaceable hood is removable for sterilization, while the fluorescence excitation LEDs stay on the scanning device.

19. The apparatus of claim 13, wherein an excitation wavelength is below 350 nm, and a wavelength of an illumination pattern is in a range of 365 nm-405 nm.

20. The apparatus of claim 1, wherein the scanning device is adapted to use, in the second imaging modality, light in a red wavelength range for excitation of porphyrins and the at least one processor is configured to overlay a fluorescence image over the 3D data of the 3D scan.

21. The apparatus of claim 1, wherein the scanning device has one or more combinations of the following imaging modalities:

use of visual wavelength 2D images together with 3D information used for recalculation of a magnification, distance and angulation of the lesion;

visual wavelength 2D image overlaid over a 3D texture image of the lesion;

use of visual wavelength 2D images and fluorescent image with 3D information used for recalculation of a magnification, distance and angulation;

visual wavelength 2D image and fluorescent image overlaid over a 3D texture image of the lesion;

visual wavelength 2D image overlaid over a 3D texture image of the lesion and a subsurface structure image;

visual wavelength 2D image and fluorescent image overlaid over a 3D texture image of the lesion and a subsurface structure image.

22. The apparatus of claim 1, wherein an artificial neuronal network is integrated into the apparatus, and adapted to use images of a multimodal image database for training, and classifying multimodal images which are fed in the artificial neuronal network.

23. The apparatus of claim 1, wherein the 3D information is sent by a computer to a cloud-based artificial neuronal network for training of the cloud-based artificial neuronal network, and collected in a multimodal image database, wherein the cloud-based artificial neuronal network is connectable by the apparatus for classification of intra-oral lesions captured by the apparatus and provided to the cloud-based artificial neuronal network.

24. The apparatus of claim 22 or 23, wherein additionally to the 3D information, other information including palpation results, removability of whitish layers, lesion history and risk factors such as smoking, or alcohol is used for training and retrieval of the cloud-based artificial neuronal network.

25. The apparatus of claim 1, wherein the scanning device comprises one InGaAs image sensor configured to cover at least a wavelength range from 1000 nm-1600 nm.

26. The apparatus of claim 1, wherein the scanning device comprises a CQD image sensor configured to extend sensitivity into a near-infrared (NIR) range covering at least additionally a wavelength range from 1000 nm-1400 nm.

27. The apparatus of according to claim 1, wherein the at least one processor is configured to additionally provide the 3D information on the distance and angulation between scanning device and the dermis or mucosa through use of an illumination pattern, a stereogrammetry, or time of flight.

28. A method for multimodal imaging of a dermal or mucosal lesion comprising:

computing images from raw data provided by a scanning device having illumination light sources and sensor, the scanning device adapted to use at least two imaging modalities from which a first imaging modality generates 3D data for a 3D image in a 3D scan of the dermal or mucosal lesion, the scanning device having illumination light sources, a beam splitter, and sensors, the sensors including a visible light 2D sensor and an infrared light 3D sensor, and the beam splitter being configured to spectrally split detected light into wavelengths appropriate for the visible light 2D sensor and the infrared light 3D sensor, computing 3D information on a distance and an angulation between the scanning device and a dermis or mucosa, and mapping at least an image generated by a second imaging modality over the 3D image of the 3D scan based on the 3D information.

\* \* \* \* \*